United States Patent [19]

Hindle

[11] Patent Number: 5,327,770
[45] Date of Patent: Jul. 12, 1994

[54] APPARATUS FOR SAMPLING A MATERIAL TRAVELLING PAST A SAMPLING REGION

[75] Inventor: Peter H. Hindle, Hatfield Peverel, England

[73] Assignee: Infrared Engineering Limited, Essex, England

[21] Appl. No.: 895,337

[22] Filed: Jun. 8, 1992

[30] Foreign Application Priority Data

Jun. 10, 1991 [GB] United Kingdom ................ 9112397

[51] Int. Cl.$^5$ ............................................. G01B 11/06
[52] U.S. Cl. ...................................................... 73/1 J
[58] Field of Search .............. 73/1 R, 1 DV, 1 J, 863; 198/339.1, 340; 250/252.1; 356/243

[56] References Cited

U.S. PATENT DOCUMENTS

| | | | |
|---|---|---|---|
| Re. 34,070 | 9/1992 | Regimand | 73/1 R |
| 3,698,238 | 10/1972 | Wall et al. | 73/1 R |
| 3,719,948 | 3/1973 | Mueller | 343/757 |
| 3,878,373 | 4/1975 | Blum | 250/252.1 |
| 4,309,611 | 1/1982 | Tanaka et al. | 250/363 |
| 4,309,615 | 1/1982 | Kowalski | 260/445 T |
| 4,374,326 | 2/1983 | Wykes et al. | 250/252.1 R |
| 4,590,801 | 5/1986 | Merhav | 73/505 |
| 4,596,952 | 6/1986 | Goff et al. | 73/1 J |
| 4,698,996 | 10/1987 | Kreft et al. | 73/1 J |
| 4,712,426 | 12/1987 | Peters | 73/510 |
| 4,748,400 | 5/1988 | Typpo | 73/1 R |
| 4,986,108 | 1/1991 | Wilde | 73/1 R |

FOREIGN PATENT DOCUMENTS 1378303 12/1974 United Kingdom .
2027191A 2/1980 United Kingdom .
2068113A 8/1981 United Kingdom .

OTHER PUBLICATIONS

Web-gaging alternatives proliferate with new multiple-sensor systems (Modern Plastics International, Dec. 1989).

Primary Examiner—Robert Raevis
Assistant Examiner—Daniel S. Larkin
Attorney, Agent, or Firm—Cumpston & Shaw

[57] ABSTRACT

A sampling system includes a plurality of sensing means (3) mounted on one or more beams (2) which reciprocate, over a moving web (1) of material. The sensing zones of adjacent sensing means (3) trace out scanning paths which periodically overlap in a sampling region. One of the sensing means (primary) scans over a known reference to update its calibration periodically or continuously and this is transferred to the other sensing means (secondary) effectively via the travelling material (due to the overlap). Calibration is performed by signal processing means, storing and comparing monitoring signal levels or corresponding digital values derived at positions of overlap and making computations for the purpose of calibration. With sufficient overlap of the scanning paths any one of the sensors can be made redundant. Alternatives include sensing means which move relative to other sensing means as well as rotary arrangements.

25 Claims, 5 Drawing Sheets $f_4$ e     c     f     d     g a Zone measured by sensor 'a'
b Zone measured by sensor 'b'

Dotted lines show approx. edges of web

APPARATUS FOR SAMPLING A MATERIAL TRAVELLING PAST A SAMPLING REGION

This invention relates to apparatus for sampling a material travelling past a sampling region across which a plurality of sensing means are arranged at spaced intervals. The sensing means have respective sensing zones in the sampling region and relative movement is caused between the sensing means and the sampling zone, so that the sensing zones trace respective scanning paths over the material during each cycle of movement. Monitoring signals are derived from the sensing means which represent a characteristic of the material (such as its thickness) travelling past the sampling region. Signal processing means are used to process the monitoring signals, or values corresponding thereto to provide an output which enables the characteristic to be monitored. The invention may be used, for example in making thickness, or moisture content measurements of e.g. paper, or a thin film which is produced continuously, the paper or film being transported by rollers to a winding reel. It could also be used, for example, to determine the nature of materials which are fed onto and transported by a conveyor belt, for example, to determine the constituents of certain food products.

The material is sampled to determine a particular characteristic and the term "characteristic" is used herein to denote a property or the nature of the material. For example, a property would include film thickness, moisture content, dilution, reflectivity, transmissivity, colour or some other measurable variable. The nature of the material may be, for example, its composition, as in a mixture of substances transported by a conveyor belt. The material may be in any suitable form in which it can be made to travel past the sampling region for analysis.

The type of sensing means used will depend on the form and content of the material and on the way in which measurements can be made in order to derive information concerning the characteristic to be determined. Typical sensing means operate by detecting electromagnetic radiation (e.g. infrared sensor), or particles (e.g. beta-particle sensors) either of which can operate with regard to a transmissive or reflective property of a material. In some cases, the sensing means will include a source e.g. of radiation, or a generator, e.g. means for generating a magnetic or electric field, as well as a sensor. However, other forms of sensing means may not require such a source or generator.

U.S. Pat. No. 3,621,259 discloses apparatus comprising a source of infrared radiation and a sensor mounted in a head supported for reciprocal movement on a beam or frame which spans a continuously produced web. The head is caused to reciprocate over the web approximately at right angles to the direction of web movement, the head moving at a constant speed across the web. The beam or frame supporting the head may be a straight single beam which passes over the path of web movement, and which supports the source of radiation and the sensor. Alternatively, it may be a C-shaped, or O-shaped frame which encompasses the path of web movement so that the source and sensor can be on opposite faces of the web. These beams or frames are expensive to produce because a high level of mechanical performance is required at fast scanning speeds and they must survive continuous usage under arduous conditions of industrial environment and yet still maintain high positional accuracy for the head or heads. Different devices can be used to drive the heads across the beams or frames but these devices are usually lead-screws, drive belts, cables or chains driven by electrical motors. As the head reciprocates, its sensing zone defines a zig-zag sensing path on the moving web so that only local portions or samples of the material are scanned as it travels past the sampling region. The sensing zone is generally a well defined target determined by the construction of the sensor and it may define an area of, for example, 10–100 mm$^2$ on the face of the web to provide the necessary measuring resolution.

With the passage of time, production lines have been driven at increasing speeds. As the line speed increases the latter type of sensing head senses less of the web unless the sensing head is made to reciprocate at a faster speed. For example, the head needs to move at some 20 meters per minute to allow a web having a width of 10 meters to be scanned in approximately 30 seconds. Whilst this can accommodate web speeds of up to 500 meters per minute, between 250–500 meters of material will pass under the head over each reciprocating cycle. However, less time will then be available for the head to make each sample measurement, e.g. over small fractions of a second, and hence the known system then provides statistically less representative samples of the moving web. If inaccurate measurements are made, thousands of meters of material can be wasted, and production time can be lost. Production time will also be lost if a single sensing means fails and needs to be replaced.

As an alternative to a reciprocating head, attempts have been made to mount a plurality of fixed sensing means at spaced intervals on a beam but this arrangement has various limitations. An example of such a system is described in Modern Plastics International, December 1989, Page 16. Whilst this arrangement avoids the need for reciprocation, there are various other problems.

As the individual sensing means are fixed at spaced intervals, the sensing zones of adjacent sensing means will scan strips of the web which are at fixed transverse locations across the web, and these strips will be separated by "dead" areas which are not sensed. Therefore, the outputs of the fixed heads do not provide a representative sample taken across the full width of the web.

A further problem is that there is no provision for checking the calibration of the fixed heads once they have been initially calibrated and put into operation. As there is no easy way to check the calibration of the heads periodically, when they are in use, there is always uncertainty about the accuracy of the measurement.

In order to ensure accuracy of measurement, it is necessary for each sensing means to be of high quality, for example, the system may contain an array of beta gauges and this contributes appreciably to the cost of the apparatus. Moreover, if individual beta gauges need to be removed for maintenance, repair or a calibration check, then the coverage by such a gauge will be temporarily lost whilst the production of a moving web continues. This can lead to problems where a local change in web thickness occurs in a region which is not being sensed.

GB-A-2 027 191 discloses apparatus for detecting faults in a travelling sheet of fabric and it uses a scanning device with a linear array of reciprocating sensors which trace out overlapping scanning paths on the fabric. However, individual sensors produce individual signals for detecting faults in respective portions of the fabric. GB-A-2 068 113 relates to GB-A-2 027 191 but discloses a special sensor arrangement for reducing errors due to variations in illumination. GB-A-1 378 303 discloses apparatus which includes two stationary detectors and a reciprocating optical system which causes a beam of radiation to traverse a moving web of paper. A beam splitting arrangement directs some of the radiation into one of the stationary detectors, without passing through the web of paper, so as to provide a reference signal. The other detector receives radiation which has passed through the web and produces a measurement signal. A comparator compares the reference signal with the measurement signal. The apparatus seeks to solve a problem due to errors caused by thermal stress and bending of supporting structures in warm locations and the reference signal is used for measurement purposes only (not calibration).

The problem facing the invention is to provide an arrangement for accurately sensing a characteristic of fast moving material without the problems of the prior art, particularly the problem of providing accurate data for a representative sample of a web moving at high speed without necessarily incurring the cost of expensive sensing means, or needing to stop for calibration, or because a lack of coverage occurs due to a faulty or missing sensing means.

In accordance with the invention, the sensing means includes at least one primary sensing means which produces comparatively accurate monitoring signals compared with the monitoring signals produced by the other or secondary sensing means. The signal processing means also includes means for storing and comparing the monitoring signals or values corresponding thereto, which are produced where the scanning paths overlap. The processing means processes the signals or values and produces information, for the signal processing means, either for calibrating the secondary sensing means with respect to the primary sensing means and the material travelling past the sampling zone, or for making any one of the sensing means redundant, or both.

One advantage of this arrangement is that where the scanning paths overlap, the respective monitoring signals, or values corresponding thereto, can be used by the signal processing means to enable the secondary sensing means to be calibrated with respect to the primary sensing means and to the material passing the sampling zone. The primary sensing means can be used to derive an accurate signal and this is then used, as a reference, for the purpose of calibrating the secondary sensing means.

The system may be analogue, digital, or a combination of both, whereby the signal processing means stores and compares analogue signal levels, or digital values depending on the circuitry used. For example, circuitry is currently available for storing a multiplicity of analogue signal levels and these could be handled by analogue circuitry or processed in order to determine calibration factors for the secondary sensing means. Alternatively, the monitoring signals may be converted into digital values which can be stored and processed independently of the real time operation of the scanning array. This is advantageous where, for example, monitoring signals derived at instants of time are collected over a predetermined period (e.g. several cycles of relative periodic movement) and then averaged to provide mean values for the purpose of computing statistically improved calibration factors. This may be achieved by comparing mean values and variances of the monitoring signals produced by adjacent sensing means.

The primary sensing means may be a highly accurate measuring instrument, such as a beta gauge or infrared gauge, which can be used to provide an absolute value of measurement of the material passing the sample zone. The processing means then uses this value as a reference for calibrating the other secondary sensing means. However, a particular advantage of the invention is that the primary sensing means need not be a high grade instrument, since it may be made to scan a known reference, such as a sample of the material having a range of known characteristics, in order to derive an accurate signal which is used as the basis for calibrating the secondary sensing means. For example, the primary scanning means can periodically scan off the edge of the travelling web, so that its sensing zone scans over a known sample of the same material which has, e.g. a range of accurately known material thicknesses. The primary sensing means can then be periodically recalibrated each time it scans the known thicknesses of the reference material. However, the primary sensing means need not be part of an array of cyclically moving secondary sensing means, because the primary sensing means could be fixed adjacent the edge of the travelling web so that it continuously scans a reference material so as to provide the accurate signal, the next adjacent secondary sensing means periodically scanning the same reference so as to derive a set of monitoring signals for comparison with a corresponding set of monitoring signals derived by the primary sensing means, hence enabling the calibration technique to be initiated. With the reference means, none of the sensing means needs to be an expensive high grade instrument, as long as it is stable over a reasonable period of time, e.g. a predetermined number of cyclic movements which enables the relevant monitoring signals to be collected, stored and processed for satisfactory calibrations. This is a distinct advantage over prior art techniques which require high grade instruments that remain stable for long periods of time due to the absence of calibration.

In a specific embodiment of the invention, the sensing means may be capacitance sensors or relatively inexpensive infrared sensors, which may otherwise be considered to be inadequate for sampling a web of material travelling at high speed. In effect, these less expensive sensing means can be used because the invention provides continuous or dynamic calibration. (The term "calibration" is used herein to include different forms of signal adjustment, e.g. such as those made for the purpose of standardisation, correction of measured values over a range of measuring values, correction for zero drift, etc.).

As indicated above, the invention is not confined to the use of digital techniques since analog circuitry may be used to achieve a similar purpose. In some cases, this may be advantageous in simplifying the system, since the previous trend has been towards reducing analog circuitry to the point of measurement, i.e. the sensor, and deriving digital values as early as possible in order to use microprocessors to manipulate the digital values and to compute the required results. The invention may be embodied in a way which tends to reverse this trend, e.g. by providing a better compromise between analogue and digital techniques in collecting and processing signals and/or data in order to achieve the required result. Generally speaking, signals and/or values may be stored over several cycles of movement in order to collect enough raw data which can then be analysed, by suitable statistical techniques, to derive mean values which are processed to provide the required calibration factors. Mean values improve accuracy and different algorithms may be employed in order to refine the calibration techniques.

Calibration often involves the derivation of what may be termed "span" and "zero correction" factors which compensate respectively for the relative sensitivities of the sensing means and the amount by which each sensing means needs to be corrected for zero drift. In the former case, where the sensitivities of the sensing means each bear a known relationship with the parameter to be measured, the stored values derived from a sensing means with low sensitivity will need to be multiplied by a high span factor, and vice versa. In the case of zero correction, a zero correction factor may be added or subtracted from the value of the signal derived by a particular sensing means. This is a rather generalised simplification of the process which is carried continuously in the sampling system, because the data collected over several cycles in the given time period needs to be related to the interleaving of the scanning zones of the adjacent sensing means and this process is continuous in the sense of, for example, a rolling average, or exponential function, due to the continuous process of producing the travelling web and making the sampling measurements. Therefore, statistical analyses will depend on continuous variabilities in the measured characteristics of the travelling material and will hence need to be selected in accordance with particular requirements.

A further advantage of the dynamic calibration technique of the invention is that the secondary sensing means need not be pre-calibrated before they are used in the scanning array. For example, after the system has been initially running for a given period of time, distinct signal values would have been stored for each of the secondary sensing means and these will be related to the signal values of the primary sensing means so that the monitoring signals from all of the sensing means yield accurate measurements. This is due to the frequency of the dynamic calibration, since the calibration of the primary sensing means, which is shared to the secondary sensing means, is continuously updated.

In a preferred form of the invention, relative movement is caused between a plurality of sensing means and the sampling region. More particularly, the sensing means are mounted in one or more arrays which move transversely across the path of the travelling material. For example, with a single linear array which reciprocates over the travelling material, the sensing zones of adjacent sensing means intermittently correspond with similar areas in the sampling region. The amplitude of reciprocation needs to be at least sufficient to enable the scanning track of any one sensing means just to overlap with the scanning track of an adjacent means, i.e. at the limits of reciprocation. In this way, adjacent sensing means periodically cover the same area in the sampling zone, although they will each sense a different area of the travelling material due to its continuous movement through the sampling zone between reciprocating movements of the scanning array. This makes no significant difference if the characteristics of the material change slowly with time. However, even in this simple case, there is a problem that calibrations can be degraded due to sequentially comparing signals starting at one end of the array and moving step by step towards the other end of the array. One way of reducing or eliminating this problem is to have, for example, two linear arrays of equally spaced sensing means, the arrangement being such that corresponding pairs of sensing means (one on each array) periodically align so that their sensing zones cover the same, or closely adjacent areas in the sampling zone. In some cases, to prevent cross-talk, corresponding pairs of sensing zones need to be kept slightly apart. For example, when using optical techniques, it is important to prevent stray radiation from being scattered or reflected into the wrong sensor. With this "parallel" arrangement, it is possible to obtain greater accuracy.

Linear arrays are not essential because there may be circumstances where rotary arrangements can be used instead. For example, a primary sensing means may rotate relative to a plurality of fixed secondary sensing means which have contiguous sensing zones in the sampling region. Alternatively, a plurality of secondary sensing means may rotate relative to a first primary sensing means, or there may be counter-rotation between primary and secondary sensing means. Moreover, there is no need for a primary sensing means where each of the sensing means, e.g. in a rotary head, scans off the travelling material in order to sense the same reference in cyclic rotation.

In any of these cyclically moving arrangements where a plurality of sensing means move over the travelling material, a lower scanning speed and a small amplitude can be used compared with a single scanning head. This not only relieves the problem of having less time for making measurements, but also means that less expensive drives can be used.

The sampling system may be made even more efficient by providing more than one reference which is scanned by respective sensing means in a scanning array. For example, in a reciprocating arrangement, the two sensing means adjacent the edges of the travelling material can be made to scan respective reference means located at each side of the travelling material. In this way, in a single linear array, calibration can effectively pass simultaneously from both ends towards a mid-point of the array. In the case of using, for example, parallel pairs of reciprocating arrays, the outside sensing means can scan respective edge references whilst a first set of corresponding pairs of sensing means align. The reference calibration can then be used, in the next half cycle of movement, when a second set of corresponding pairs of sensing means align. This enables simultaneous calibration throughout the array.

In order to improve the sampling system still further, the amount by which the scanning paths of adjacent sensing means overlap or are interleaved can be increased so that larger amounts of the travelling material are sampled to provide more sets of signal levels or digital values which can then be averaged and processed to achieve calibration. Whilst this imposes a greater load on processing data, due to dealing with far more sets of monitoring signals (i.e. from similar areas in the sampling region) suitable strategies and algorithms may be used for statistically analysing the data to provide high measurement accuracy. In this way, there is little or no risk of incurring cumulative errors due to traversing the travelling material in order to collect reference and measurement data for the purpose of calibration. With a greater overlap or interleaving of the scanning paths, it is more important to relate the monitoring signals from adjacent sensing means with regard to similar areas on the travelling material. In the case of using a simple linear reciprocating array, monitoring signals can be collected at the ends of reciprocal movement, where the sensing means pause or dwell for short instants whilst measurements are made. Whilst the sensing means will also dwell at the ends of reciprocal movement with a greater overlap between adjacent scanning paths, the sensing means will be moving therebetween and the sensing zones of each sensing means will cover a short track i.e. depending on the speed of material movement and the speed of reciprocation of the scanning array. However, this may be of little or no consequence, depending on the application of the sampling system and the speed at which measurements can be made.

In the case of one or more reciprocating arrays, individual sensing means will trace out zig-zag scanning paths on a web of moving material. The zig-zag paths may be considered to be made up of sequential chevrons, alternate ones of which correspond with the scanning paths each of the adjacent sensors. If these alternate chevrons are fully aligned in the direction of web movement, i.e. so that the scanning paths of adjacent sensing means totally overlap (in other words, the chevrons are fully interleaved), the monitoring signals may be compared over greater portions of the travelling material. Besides the advantage of providing far more raw data which, with suitable processing, yield much higher accuracy, this degree of overlapping or interleaving of adjacent scanning zones has the further advantage of providing redundancy in the sampling system. For example, where the sampling zones of adjacent sensing means are moved so that they trace out scanning paths which overlap by one half of their amplitude, the central sensing means in a sequential set of three sensing means is effectively redundant. The signal processing means can be then made to ignore the signals from a defective redundant sensing means so that sampling can continue without having to stop to replace the defective sensing means. This redundancy aspect is a particular advantage in industries where materials are continuously produced, or are supplied to transporting means, such a conveyor belt, since any downtime results in a waste of material besides the loss of production time and is therefore expensive.

The redundancy aspect of the invention may be exploited independently of the calibration aspect of the invention. However, in preferred embodiments of the invention, both the redundancy aspect and the calibration aspect are exploited in the same system. A further advantage of the redundancy aspect is that any one sensing means in an array of sensing means can be periodically removed, so that it can be serviced and then refitted, or simply replaced with another. In order to facilitate this, the sensing means may comprise plug-in modules which can be easily removed and refitted.

The calibration aspect and/or the redundancy aspect of the invention may be embodied in various ways. Some of the features of such embodiments will now be described on the understanding that they be adapted, as required, for the purpose of either calibration, or redundancy, or both, to suit the intended purpose.

Sensing means, such as infrared sensors may be mounted on a movable support, such as a beam, which is caused to reciprocate across the direction of material travel. Alternatively, respective arrays of sensing means may be mounted on parallel supports which reciprocate in opposite directions. In a further alternative, one support may be fixed whilst the other reciprocates. The extent of reciprocation may allow the "edge" sensing means to move beyond the edge of the travelling material so as to scan reference means adjacent one or both edges of the travelling material. However, one sensing means may be fixed over reference means whilst the next adjacent sensing means has a scanning path which overlaps the reference periodically to allow for calibration.

Instead of using reciprocation, the sensing means may be mounted on a rotary support which rotates in the parallel plane above the plane of material movement. Adjacent sensing means then scan similar portions of the sampling region in sequence. This arrangement would also be appropriate for use with material transported in cylindrical form. Primary sensing means may be fixed relative to secondary sensing means on a rotary head so that each of the secondary sensing means passes by the primary sensing means during a cycle of rotation. Alternatively, a primary sensing means may be made to rotate with respective to fixed secondary sensing means, or primary and secondary sensing means may be mounted on respective supports rotating in opposite directions. A similar effect can be achieved in a reciprocating arrangement by causing a primary sensing means to scan backwards and forwards passed fixed, or oppositely moving, secondary sensing means. Such arrangements also provide for redundancy if one of the moving sensing means is used to provide monitoring signals in place of a defective secondary sensing means.

In the case of using, for example, two, oppositely reciprocating supports, the supports may be mounted on the same side of the travelling material. The sensing means on such supports may have sensing zones which are adjacent to one another on the face of the travelling material. However, the sensing means may be slightly tilted so that their sensing zones correspond on the face of the travelling material (if this does not lead to any adverse cross-talk). One array of sensing means may also be mounted above the travelling material and another array of sensing means may be mounted beneath the travelling material.

The sensing means can alternatively be mounted on swivels on a fixed support or supports, and drive means may be used to move the sensing means pivotally, or rotationally, to scan respective portions of the sampling region.

With regard to the way in which the monitoring signals are collected, stored and processed, this will depend on the way in which the sensing means are supported and made to scan different portions of the sampling region. In some cases, there will be a time lapse between the monitoring signals derived at similar locations in the sampling region, i.e. where the scanning paths overlap. In other cases, adjacent pairs of sensing means will simultaneously sense similar or closely adjacent areas of the travelling material and there will be little or no time lapse between the respective monitoring signals used for the purpose of checking the calibration. The nature of the sensing means will depend on the measurements to be made and on the nature of the material. For example, if the material is transparent or effectively transparent, e.g. to electromagnetic radiation or to nuclear particles, then infrared scanners or beta gauges can be used. Alternatively, if the material reflects radiation, its reflectivity, instead of its transmissivity, can be measured. However, other sensing means may be employed, such as those used in determining changes in the dielectric constant of a material, e.g. as in the case of capacitance sensors. In some cases, sensing means which have some risk attached to their operation (such as beta gauges) may be replaced with sensing means where no such risk is present. Alternatively, the primary sensing means, such as a beta gauge, could be safely housed in a fixed position whilst comparatively safer secondary sensing means have scanning paths external to the beta gauge housing, as long as one of the secondary sensing means periodically scans a portion of the sampling region of the primary sensing means.

It will be understood that the sensing means normally produce monitoring signals by scanning bands of the travelling material which are at least contiguous, if not overlapping. These monitoring signals are generally used for measuring characteristics of the material across its entire width and hence taking a representative sample for the purpose of measurement or control. Digital or analog values corresponding to the monitoring signals are stored and processed for the purpose of deriving outputs for driving a display which, for example, depicts a measurement profile across the width of the travelling material. The sensing means may be of the known kind where rotating filter wheels cause intermittent beams of radiation to be directed at the travelling material so that monitoring signals are produced at consecutive instants of time. Where the monitoring signal is a continuous signal, which varies with changes in the characteristic to be measured, known sampling circuitry or processing techniques may be used to provide consecutive signal values which are stored for processing.

The monitoring signals may also be used for the purposes of alarm and/or control with regard to the continuous manufacturing process of a web. Since the techniques of processing the monitoring signals for this purpose are generally known, no further explanation need be given.

Clearly, some or all of these monitoring signals will be used for the purpose of calibration and/or redundancy and hence they will be differently processed. The selection and/or manipulation of such signals may be achieved by conventional techniques so they may be processed, in accordance with suitable algorithms, in order to effect calibration and/or redundancy. In the case of redundancy, the signal processing means can be made to ignore the monitoring signals which are derived by a defective sensing means and to use instead the monitoring signals of adjacent sensing means, or a sensing means which travels past the defective sensing means, so that the defective sensing means can be effectively removed from the system without affecting the sampling process. This is particularly advantageous in not having to stop a continuous process whilst a defective sensing means is replaced.

Embodiments of the invention will now be described with reference to the accompanying schematic drawings in which.

Figure 1:
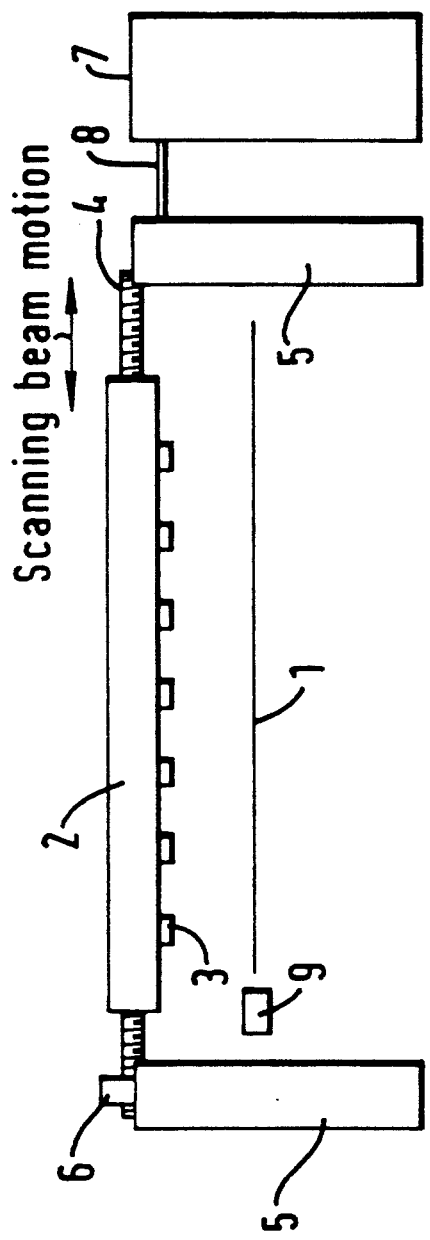
FIG. 1 is an elevation of a "single-sided" scanning apparatus in accordance with an embodiment of the invention.

Referring to FIG. 1, material in the form of a web 1 (seen in cross section) travels along a path passing through a scanning region beneath a beam 2 which supports a plurality of sensing means 3. The beam 2 is mounted on a transverse lead screw 4 which is rotatably supported, at each side, by pillars 5. Drive means 6, mounted on one of the pillars 5, causes reciprocal motion of the beam 2 and hence of the sensing means 3, during each scanning cycle, above the path of movement of web 1. The drive means 6 includes an electrical motor (not shown) for rotating the lead screw 4, but other forms of drive are possible. Signal processing means 7, including a microprocessor, display means and recording means is connected, via a cable 8 which passes through the pillar 5 and adjacent the lead screw 4 into the hollow beam 2, is connected to each of the sensing means 3. The signal processing means 7 is described in more detail below.

Figure 2:
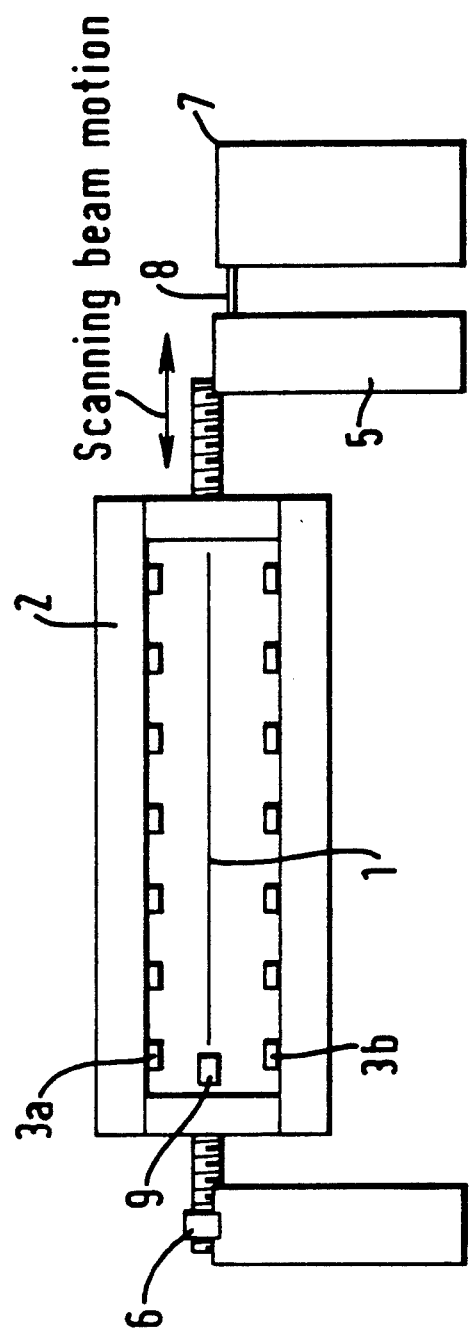
FIG. 2 is an elevation of a "double-sided" scanning apparatus in accordance with another embodiment of the invention.

FIG. 2 shows a similar arrangement except that beam 2 is of an O-shaped frame and encompasses the web 1. Linear arrays of sensing elements 3a, 3b are mounted on upper and lower portions of the frame above and below the web 1. In this embodiment, sensing elements 3a are sources of infrared radiation and elements 3b are photoelectric detectors which receive the radiation transmitted through the web 1.

In the arrangements of FIGS. 1 and 2, the sensing elements 3 (3a, 3b) may be mounted on hollow beams to house and to protect and, if necessary, thermally stabilise the individual sensing elements. However, this is not always necessary.

The sensing means 3 may be of the same type, or they may be of different types. As will be explained below, at least one sensing means 3, in the scanning array, may be considered to be a primary sensing means, and the other sensing means may be considered to be secondary sensing means. The primary sensing means is used to derive accurate signals which are used as a basis for calibrating the secondary sensing means. One way of achieving this is to cause the beam 2 to reciprocate sufficiently so that one of the edgemost sensing means, i.e. the primary sensing means, scans off the edge of the web 1 and then over reference means 9 which is, for example, a sample of the same material of the web, but having a range of known characteristics, such as different known thicknesses. This enables the primary sensing means to be initially calibrated so that its measurements can then be used by the processing means for calibrating the secondary sensing means, hence enabling the array to produce accurate measurements across the entire width of the web 1. This is achieved by having a sufficient amplitude of reciprocation to cause the sensing zones of adjacent sensing means to overlap, i.e. the limits of the scanning paths overlap (as explained below) and by appropriately sampling, storing and manipulating the monitoring signals by the processing means 7. The amount of overlap or interleaving of the scanning paths determines the amount of information which can be gathered for the purpose of calibration but, in general, it enables the web 1 to be effectively used as a means of passing on, or comparing the monitoring signals of adjacent sensing means so that the calibration of the primary sensing means can be used as a basis for calibrating the secondary sensing means. This is explained in more detail below.

Instead of using a reference means 9 to calibrate the primary sensing means, the primary sensing means can be a highly accurate and stable instrument, such as a beta gauge or an infrared gauge, either of which is capable of providing an absolute measurement (e.g. a film thickness of the web 1), or of providing an accurate measurement after being precalibrated. The primary sensing means can then be used as a reference, by the processing means 7, for calibrating the secondary sensing means. However, the advantage of using reference means 9 is that the calibration of the primary sensing means is continuously up-dated and this can be continuously transferred across the web for continuously calibrating the secondary sensing means. In this way, it is not essential to have a particularly expensive or specially made instrument as a primary sensing means, as long as it is stable over e.g. several scanning cycles. It would of course be preferable to use highly accurate primary sensing means which are highly stable over long periods of time but, where there are harsh environmental conditions and/or where cost is a significant factor, the invention enables inexpensive sensing means to be used, particularly where the calibration of the primary sensing means is continuously up-dated with respect to reference means 9. Generally, the choice of sensing means will be dictated by the field of application, the required accuracy, the material to be measured, the measuring environment, and the cost.

The sensing means may be of a known kind which produces a train of monitoring signals (e.g. as a filter wheel rotates) so as to produce values which are stored and then processed. Alternatively, the sensing means may produce a continuous output and where known sampling circuitry and/or processing techniques can then be used to provide values which are stored and processed.

Figure 3:
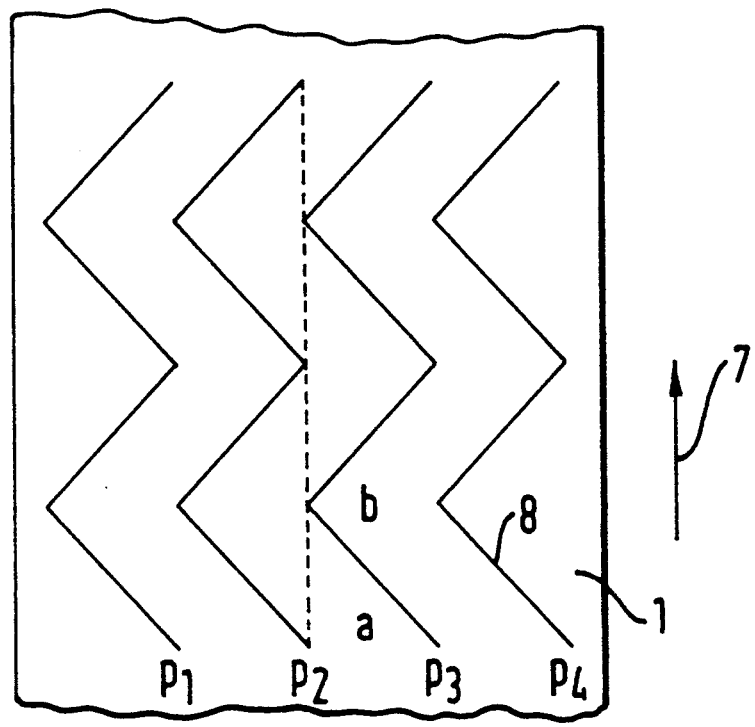
FIG. 3 is a plan view of a scanning pattern which may be produced by the sensing means in the embodiment of FIGS. 1 or 2.

FIG. 3 shows a pattern of scanning paths $p_1$-$p_4$ traced out by the sampling zones of four sensing means (not shown) mounted on structures similar to those shown in FIGS. 1 and 2. In the plan view, the web 1 moves in the direction of arrow 17 as the beam 2 (not shown) is reciprocated. The sampling zones therefore trace out zig-zag scanning paths $p_1$-$p_4$. Each path is diagrammatically represented by a line, although it will be a strip which has a width corresponding with a diameter, or width dimension of the sampling zone of the respective sensing means 3. FIG. 3 illustrates an example where the sensing means are equally spaced on the beam 2 and the amplitude of reciprocation causes adjacent scanning paths just to overlap at the reciprocating boundaries. In other words, the troughs of one scanning path ($p_2$) align with the peaks of an adjacent scanning path ($p_3$). This is differently shown in FIG. 3a which is an enlargement of the fixed sampling region scanned by the sensing means and showing how the sensing zones of adjacent sensing means just overlap, in the cross-hatched region R, at the boundaries of the respective scanning paths $p_2'$ and $p_3'$. Whilst the sensing means dwell for a short period at the boundaries of their scanning paths, it is not essential to have a dwell to take measurements. As the web 1 moves in direction 17 whilst the sensing means 3 reciprocates, a length of web will pass through the sampling region between points at which adjacent sensing means sense the same region R. Therefore, although the start of each scanning path (e.g. $p_2$) will not coincide with the end of an adjacent scanning path (e.g. $p_3$), the sensing means will still sense closely adjacent portions of the moving web. If the characteristics of the web which are measured change only slowly, this difference will not be significant because adjacent sensing means will measure, e.g. almost to the same web thickness. Since the web thickness can be considered to be the same, the monitoring signals of adjacent sensing means can be compared for the purpose of calibration.

Figure 3A:
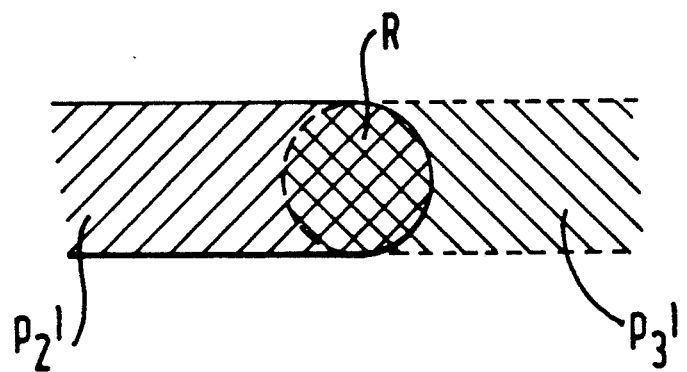
FIG. 3a is an enlarged portion of the sampling region showing a minimum amount of overlap R of the scanning paths of adjacent sensing means with such a pattern.

In the embodiment described with reference to FIGS. 3 and 3a, the scanning paths $p_1$-$p_4$ just overlap at the boundaries of reciprocation. One of the problems of this arrangement is that if any sensing means becomes defective, its monitoring signals are lost and it cannot be used to provide a "bridge" for transferring the calibration along the linear array. Moreover, the amount of data available for calibration purposes is confined to the overlap at the boundaries of reciprocation. These problems can be dealt with by increasing the overlap of the scanning paths as will now be explained with reference to FIGS. 4, 4a and 5.

Figure 4:
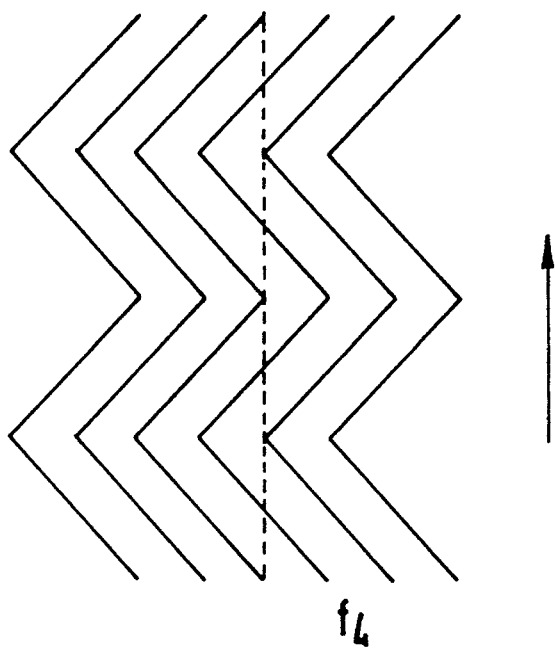
FIG. 4 is an improved scanning pattern for the sensing means shown in FIGS. 1 or 2.
Figure 4A:
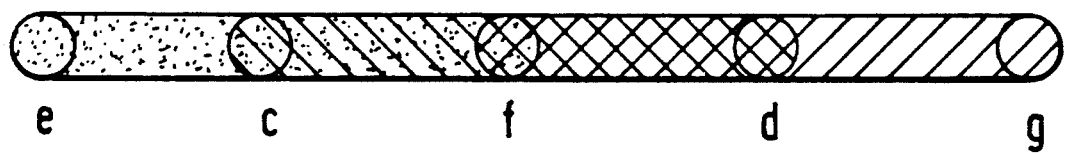
FIG. 4a is an enlarged portion; in this case the overlap being greater for adjacent scanning paths.
Figure 5:
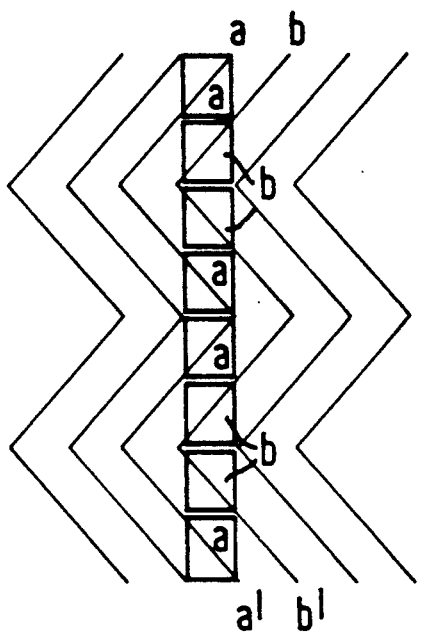
FIG. 5 is another plan view of the scanning pattern to illustrate a sampling technique with a total overlap.

In the arrangement shown in FIGS. 4, 4a and 5 the scanning paths of adjacent sensing means overlap by an extent which effectively enables any one sensing means to be redundant. FIG. 4 shows repeating chevron patterns with far more interleaving than the patterns shown in FIG. 3. FIG. 4a shows the amount of overlap in the sampling region (on an enlarged scale) where, in a set of three adjacent sensing means, the central sensing means travels over the scanning path cd (its own path), but also travels over fd, which is half the scanning path fg of the sensing means on the right-hand side, as well as travelling over cf which is half of the scanning paths ef of the scanning means on the left-hand side. In effect, if the central scanning means were removed, its scanning path cd would still be scanned, half by the right-hand sensing means and half by the left-hand sensing means.

Figure 5A:
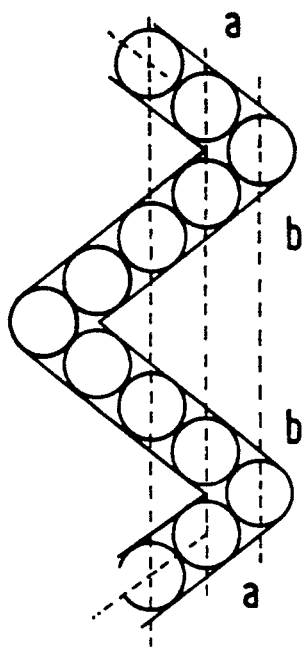
FIG. 5a is a plan view of a chevron sensing pattern.

FIG. 5 shows the same scanning pattern but with a column of boxes which represent areas common to adjacent sensors whose scanning tracks are shown as aa', bb'. The interleaving of these scanning tracks is of the form a a b b a a b b a a b b etc. The inset FIG. 5a shows one of these chevrons, on an enlarged scale, in which is shown a plurality of circles schematically representing the different sensing zones on the travelling material. Whilst circles have been used to illustrate these sensing zones, the sensing zones will be partly elongated since any one measurement occurs over a short space of time in which the web 1 travels in the direction of the arrow shown in FIG. 4. Each of these sensing zones will be aligned, in the direction of material movement, with corresponding sensing zones in a scanning pattern of adjacent sensing means. Consequently, there will be far more sampling points at which the monitoring signals of adjacent sensing means can be sampled, stored and compared to improve the accuracy of calibration. By collecting these monitoring signals over a predetermined period of time, averaging techniques and statistical analyses can be carried out in order to improve the quality of the information. For example, with 50% overlap between adjacent scanning paths in FIGS. 4 and 5, as many a's or b's (i.e. the monitoring signals corresponding to the scanning zones shown in FIG. 5a) are taken as necessary, over a predetermined number of beam reciprocations. Then the means of the a's and b's are computed and compared to perform "zero correction" adjustments of the sensing means. The variances of equal numbers of the a's and b's are also computed and matched to determine span factors which are applied by (e.g.) adjusting the gains of the sensing means.

If necessary, the signal processing means 7 can be programmed to compensate or to interpolate when there are various factors to take into account, e.g. due to differences caused by the fact that adjacent sensing means do not actually sense exactly the same piece of material as it is moved along the path, or derive signals used for calibration at similar transverse locations not necessarily at the limits of reciprocal movement. Such compensation or interpolation may take account of a slowly moving parameter, as long as its rate of change is known, i.e. with regard to web speed and the speed of sensor movement. Moreover, the signals from each of the sensing means may be summed and averaged in order to derive mean digital values used in the computations.

Clearly, different methods may be used to store analogue or digital values and to process them, in accordance with various mathematical relationships, in order to provide the required outputs. However, the signals derived from the sensing means (which may be termed "raw data") often bears a linear relationship with the parameter (e.g. thickness) to be measured. In such a case, calibration of the sensing means requires the successive operation of two numerical values on the raw data. The first of these values is a "span" value, which multiplies the raw data, so that, for example, for a sensing means with a low sensitivity, the output will be multiplied by a compensatory high "span" value, and similarly for a sensing means with a high sensitivity, by a low "span" value. The second of these values is a "zero correction" value which is usually added to the product of the "span" and the raw output, (although in some cases, the "zero correction" value may be added before multiplying by the "span value").

Figure 8:
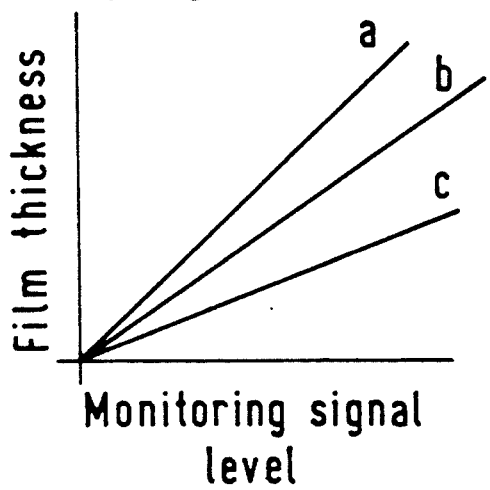
FIGS. 8 and 9 illustrate graphs to show different "span and zero values" in the case of calibrating slave sensing means with respect to master sensing means.
Figure 9:
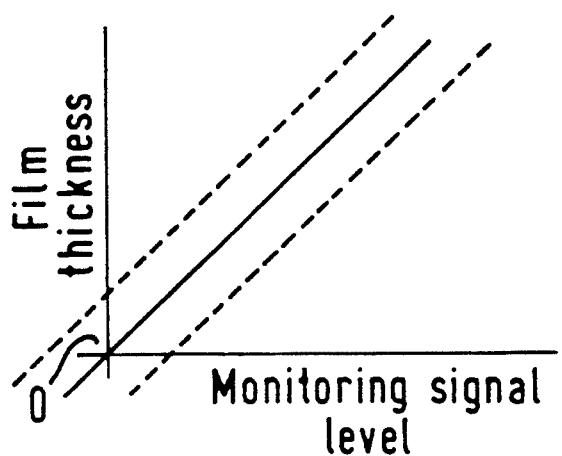

FIG. 8 schematically illustrates different "span" values for different sensing means, a, b, c, e.g. plotting film thickness against the level of the monitoring signals. FIG. 9 schematically illustrates a range (between the broken lines) for "zero correction" values, the central line being correct, i.e. no zero error.

For many categories of sensing means, the "span" value is relatively stable, and drifts in the output are predominantly attributable to changes in the "zero correction" value. Starting from a nominal calibration which may be preset, for such sensing means, an adequate transfer of calibration may be obtained by logging the calibrated outputs from both the primary or calibration donating sensing means and the secondary or calibration accepting sensing means, whenever they represent measurements taken at the boundaries of cross web (transverse) movement (see FIG. 3a) or, in the event of more deeply interleaved scanning paths (see FIG. 4a), at similar positions. After such data has been logged for a time period extending over at least several scans (but short compared with the characteristic time scale of any sensor drift) the mean calibrated outputs for both donating and accepting sensing means, are computed from the logged data. Calibration is then transferred by adjusting the "zero correction" value of the accepting sensing means by the difference between the two means.

Assuming that output data from all sensing means has been logged over the same time period, the above mentioned accepting sensing means can now become the donating sensing means, and transfer calibration to a new accepting sensing means, and the calibration transferred across the array of sensing means.

The data processing can then be restarted.

Where the data are not measured by two sensing means at the same time, as in, for example, the scanning patterns of FIGS. 3 and 4, then an improved method of calibration transfer involving somewhat greater computation is useful. By logging the output data of the sensing means output data together with either the times at which the data were measured, or the positions along the length of the web to which the data relate, it is possible to apply either a linear or a polynomial statistical line fit to the data, treating the time or length position data as the independent variable, and the parameter that is being measured as the dependent variable, where "dependent" and "independent" having their usual statistical meaning.

Integration of the lines fitted to the data from both calibration donating and calibration accepting sensing means over a common time or distance (in length) will yield an improved estimate of the mean values, especially when the parameter to be measured is exhibiting significant fluctuations during the duration of the data logging period.

When it is desired to adjust both the "span" and the "zero correction" values of the calibration, it is necessary to log output data over a period in which the parameter to be measured, and hence the sensing means fluctuate. The data must then be submitted to a statistical analysis whereby as well as the mean value, the variance, or some other statistical measure of the fluctuations is computed.

If variances of the data sets for donating and accepting sensing means are computed, the new "span" for accepting sensing means may be computed by multiplying the previous "span" by the square root of the ration of the donor variance to the acceptor variance.

Just as a comparison of the means of the two data sets provides a measure of the necessary zero adjustment, so a comparison of the variances provides a measure of the necessary "span" adjustment.

Those skilled in the art of statistical analysis will be able to provide more sophisticated statistical treatments of the logged data, involving, for example polynomial line fits and smoothing, which provide more accurate results.

Other statistical analyses may be useful in situations where, as well as having different "span" and "zero correction" requirements, the sensing means have other inherent variability. For example, where optical transmission or reflection sensors are used, with selected wavelength regions, optical production tolerances may lead to different sensing means requiring somewhat different algorithms to provide optimum measurement of the same parameter. In this case, statistical techniques such as Principal Component Analysis, or Multilinear Regression may be beneficial in providing a means for the transmission of calibration from one sensing means to the next.

In all such cases, the underlying principle is the same; the passing of a calibration from one (or more) sensing means to another (or others) based on the outputs of the sensing means during the limited times that they are sensing the parameter for the same transverse region of the sample. Sensing the same region in the longitudinal direction is desirable, but is achieved at the expense of some physical complexity. The strategies described above for sensing in the same transverse, and different (but interleaved) longitudinal regions involve more complex computation, but their physical simplicity more than compensates for this.

Besides ensuring more accurate transfer of signal data when calibrating, arrangements with sufficient interleaving of the scanning paths to provide redundancy have the added or different advantage that if one sensing means becomes defective, it can be effectively "switched out" of the circuitry because the adjacent sensing means will continue to supply the "missing" information. Such a defective sensor may therefore be replaced whilst the manufacture of web 1 continues. This is a particularly important advantage in avoiding downtime in a continuous production process where it is difficult and expensive to stop in order to make a repair and to re-start. To facilitate replacement, the sensing means are preferably plug-in modules which can be easily removed and replaced. The signal processing means may be programmed automatically to disregard the signals from a defective or removed sensing means, so that the output depends on the signals of the remaining or operative sensing means.

One potential problem with a linear reciprocating scanning array is that a degradation can occur in the transfer of calibration information along the array. Only the secondary sensing means next to the primary can be calibrated with respect to the primary, since the other secondary sensing means receive information "second hand", or "third hand" etc. as the calibration ripples through the array. Therefore, any error will be progressively handed on and, if this worsens, the calibration of the furthermost sensing means will deteriorate. This problem can-be overcome by using a "parallel" arrangement as shown in FIG. 6.

Figure 6:
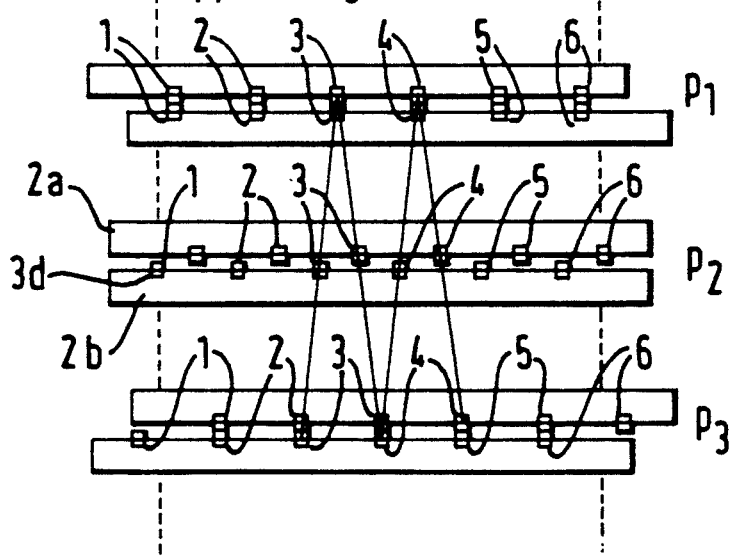
FIG. 6 is a plan view of three positions of a twin beam scanner according to a further embodiment of the invention.

FIG. 6 schematically illustrates three positions P1, P2, P3 of two arrays of sensing means 3c, 3d mounted on respective reciprocating beams 2a, 2b. Beams 2a, 2b are reciprocated in the opposite directions so that, at the ends of each reciprocating movement, different pairs (1,1 or 1,2; 2,2 or 2,3; etc.) of sensing means are in-phase and their sensing zones are aligned or coincide. This is shown at positions 1 and 3, whereas at the midway position 2, the sensing means are out of phase. Whether the sensing zones align or coincide will depend on whether there is likely to be any cross-talk, e.g. as in the case of detecting stray transmitted or reflected infrared radiation. However, in either case, simultaneous pairs of measurements can be made at closely adjacent or corresponding portions of the material 1 which is passing the sampling region. Since simultaneous pairs of measurements can be made, the calibration data is more effectively produced and it can be more effectively processed to avoid the degradation problem mentioned above in connection with a single linear array. Thus, a higher standard of calibration is ensured, which is particularly useful where large fluctuations can occur in the characteristics being measured during continuous manufacture of the web 1. It is clear that any one sensing means 3c or 3d can be made redundant if it becomes defective, although this will temporarily lose the pair coincidence of monitoring signals (or near coincidence where the scanning zones do not precisely correspond) at the position of redundancy.

The beams 2a, 2b will normally be situated so that they are on the same side of web 1. This may require the sensing means to be slightly tilted so that their sensing zones correspond on the web 1 (assuming no cross-talk), although this tilting will not be necessary if it is important to avoid cross-talk by having closely adjacent sensing zones on web 1. In the latter case, the differences in the monitoring signals, due to non-correspondence of sensing zones, would normally be considered as insignificant. so that the sensing means 3c, 3d will have respective coincident or near coincident sensing zones at particular periods of time.

The purpose of clarity, reference means 9 has not been shown in FIG. 6, but such means may be used for continuously calibrating the primary sensing means at the edge most positions of the web 1.

In an alternative arrangement (not shown), one beam reciprocates and the other beam is fixed, the amplitude of reciprocation achieving the same in-phase alignment of the sensing means but at twice the relative speed.

In a further alternative arrangement (not shown) an array of a plurality of fixed sensing means are arranged at spaced intervals on a fixed beam, and a single reciprocating sensing means is arranged to reciprocate past each of the fixed sensing means on an adjacent beam. The reciprocating sensing means would then sequentially be aligned with each of the fixed sensing means twice in each cycle of movement. However, this arrangement would suffer from the need for a high speed single sensing means compared with the single head scanning arrangement of the prior art.

Figure 7:
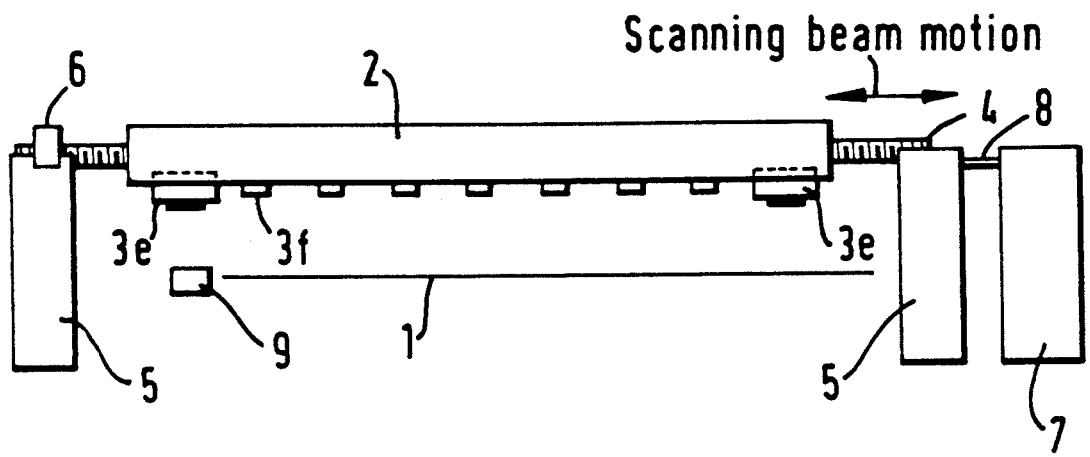
FIG. 7 is an elevation of an embodiment which employs two master sensing means, one on each side of an array of slave sensing means.

FIG. 7 illustrates an arrangement in which two primary sensing means 3e are provided at respective ends of a reciprocating beam 2 on which is mounted a linear array of spaced sensing means 3f. An advantage of using two primary sensing means 3e is that less time is required for checking the calibrations with respect to the reference means 9. Similarly, reference means 9 provided at each edge of web 1 can be used in the twin beam arrangement described in connection with FIG. 6.

The construction and detailed operation of the signal processing means 7 has not been described since its operation will be understood by those skilled in the art. In a digital system, the processing means 7 is essentially a computer which is programmed to receive signal inputs from the sensing means and to convert them into digital values which are used by appropriate programs. There may also be a data input relating to the speed of transport of the material through the sampling region, the spacing of the sensing means and the period of reciprocation. The computer will then execute the program in order to continuously calibrate the slave sensing means, with respect to the master sensing means, to allow for redundancy, and to provide outputs which are suitable for use in driving indicating or alarm means, and/or to control the process by which the transported material is continuously produced. Other data may be supplied to the computer, e.g. relating to variables and constants which are taken into account in computing corrections and/or usable values for the purpose of indication and/or control. Some variables may be related, in time, to the speed of transport of the material through the sampling zone so as to take account of relatively rapid fluctuations which change in a manner that enables interpolation of signal values to be made. Clearly, the technique or strategy used in programming the microprocessor will depend on the way in which the equipment is constructed and used as well as on the nature and purpose of use. However, the processing of the signals and the way in which they are modified by programs in the computer will be of a mathematical nature which would be understood by those skilled in the art. Although various techniques may be used, these do not detract from the underlying principle of the invention which is to cause and overlap sensing zones in the sampling region, so as to enable either the "calibration" aspect of the invention, or its "redundancy" aspect, or both to be achieved.

Generally speaking, the primary/secondary sensing means arrangement provides important cost and performance benefits. Whilst these have been mentioned above, certain aspects deserve special attention.

The array of sensing means requires only short term stability with regard its susceptibility to environmental changes, or to changes in measurement resulting from a lack of long term robustness of the algorithm since the algorithm used by the signal processing means 7 can provide measurement values depending on the design of the system.

The invention is particularly useful in measuring paper which is produced by a continuous process and fed, in the form of a web, through the sampling region. For example, a basic two or three wavelengths infrared absorption gauge can be used for measuring paper basis weight. The sensitivity of infrared measurement to filler, furnish and formation normally prohibits it from being used for basis weight measurement. However, on a given paper and for a reasonable period of time, a simple infrared sensing means will give good results when used in an arrangement according to the invention. The primary sensing means could be a beta gauge for basis weight measurement.

An array of infrared secondary sensing means are much cheaper to produce, can work at a large distance from the web and are not radio-active. Similarly, microwave sensing means could be used as the primary moisture sensing means with infrared secondary sensing means. In this case, the microwave sensing means may be fixed and one of the secondary sensing means has a scanning path which overlaps that of the primary sensing means once during each cycle of the movement.

Plastic film thickness can be measured accurately with special infrared sensing means. A capacitance measuring sensing means is cheaper but is prone to disturbances by inclusions in a product and to local temperature variations. However the invention could be used with a primary/secondary arrangement, to provide infrared and capacitance measurements. In this case, the infrared measurement is made by the primary sensing means and the capacitance measurements are made by the secondary sensing means.

In summary, important features of at least preferred embodiments of the invention are faster scanning rates, multi point measurements, frequent and automatic recalibration/standardisation, and the ability to employ simple low cost sensors which emulate the performance of much better sensors and the possibility of redundancy to avoid any downtime in continuous production processes.

I claim:

1. Apparatus for sampling a material which travels past a sampling region, the apparatus comprising:
   sensing means arranged at spaced intervals with respect to the sampling region, the sensing means having respective sensing zones in the sampling region;
   drive means for causing relative periodic movement between the sensing means and the sampling region so that, in a cycle of such movement, there is a periodic overlap of at least the sensing zones of adjacent sensing means in the sampling region due to an overlap of respective scanning paths of the sensing means, the sensing means producing monitoring signals when sensing respective adjacent portions of the material across its width, said monitoring signals representing a characteristic of the material travelling past the sampling region; and
   signal processing means for processing values corresponding with the monitoring signals to provide an output for monitoring changes in said characteristics,
   said sensing means including at least one primary sensing means which produces comparatively accurate monitoring signals compared with the monitoring signals produced by the other or secondary sensing means, and said signal processing means further including means for storing and comparing the monitoring signals or values corresponding thereto, which are produced where the scanning paths overlap, said processing means processing said signals or values and producing information which is utilised by processing means for calibrating the secondary sensing means with respect to the primary sensing means and the material travelling past the sampling zone.

2. Apparatus according to claim 1 wherein said information is also used by said processing means to make any one of the sensing means redundant.

3. Apparatus according to claim 1 wherein the secondary sensing means are of relatively lower quality than said primary sensing means and said signal processing means continuously updates the calibration of the secondary sensing means.

4. Apparatus according to claim 1 wherein said signal processing means stores monitoring signals (or values corresponding thereto) which are produced, at instants of time, by the sensing means where the scanning paths overlap and which are also produced over one or more cycles of said movement.

5. Apparatus according to claim 4 wherein said signal processing means is also capable of
   averaging the stored signals,
   computing variances of the averaged signals for adjacent sensing means, and
   comparing averaged values for adjacent sensing means and comparing variances for adjacent sensing means in order to calibrate the secondary sensing means with respect to the primary sensing means.

6. Apparatus according to claim 1 wherein sensing zone of the primary sensing means traces out a scanning path which periodically covers reference means as well as a portion of a scanning path traced out by one of the secondary sensing means.

7. Apparatus according to claim 6, in which the reference means comprises a sample of the material having a known characteristic or a known range of characteristics for providing respective reference values.

8. Apparatus according to claim 1 wherein said relative cyclic movement is sufficient to provide redundancy in any one of the sensing means, said signal processing means being further operative, as a result of comparing the monitoring signals, to adjust the required output so that a redundant sensor can be disregarded.

9. Apparatus according to claim 8, in which the sensing means have quick release connections to facilitate replacement or repair.

10. Apparatus according to claim 1, in which the sensing means are mounted on a movable support adjacent said sampling region, said drive means being used to cause reciprocal motion of said support relative to said sampling region.

11. Apparatus according to claim 1, in which the sensing means are mounted on first and second supports, said drive means causing relative reciprocation, between the first and second supports across said sampling region, the spacing of the sensing means on the supports and the amplitude of reciprocation being such that the sensing means of one support alternately align with corresponding sensing means on the other support.

12. Apparatus according to claim 11, in which the first and second supports reciprocate in opposite directions.

13. Apparatus according to claim 12 in which two primary sensing means are provided at respective opposite ends of the support or supports.

14. Apparatus according to claim 1 in which the cyclic movement is rotary movement.

15. Apparatus according to claim 1, wherein the signal processing means is operative to store the monitoring signals or corresponding values derived from each of the sensing means over a predetermined number of cyclic movements, to average said signals or values, and to make computations based on the averages for the purpose of comparison and calibration.

16. Apparatus according to claim 1, wherein the sensing means and the drive means are such that said scanning tracks of adjacent sensing means are fully interleaved and the signal processing means is further operative to store sets of monitoring signals for a multiplicity of scanning zones in said fully interleaved scanning tracks, and to average the monitoring signals, stored over one or more cycles of movement, to make comparisons of average values and to compute variances for the purpose of calibration.

17. Apparatus for sampling a material which travels past a sampling region, the apparatus comprising:

sensing means arranged at spaced intervals with respect to the sampling region, the sensing means having respective sensing zones in the sampling region;

drive means for causing relative periodic movement between at least one of said sensing means and the remaining sensing means so that, in a cycle of such movement, there is a periodic overlap of at least the sensing zones of adjacent sensing means in the sampling region due to an overlap of respective scanning paths of the sensing means, the sensing means producing monitoring signals when sensing respective adjacent portions of the material across its width, said monitoring signals representing a characteristic of the material travelling past the sampling region; and signal processing means for processing values corresponding with the monitoring signals to provide an output for monitoring changes in said characteristics, said sensing means including at least one primary sensing means which produces comparatively accurate monitoring signals compared with the monitoring signals produced by the other or secondary sensing means, and said signal processing means further including means for storing and comparing the monitoring signals or values corresponding thereto, which are produced where the scanning paths overlap, said processing means processing said signals or values and producing information which is utilised by processing means for calibrating the secondary sensing means with respect to the primary sensing means and the material travelling past the sampling zone.

18. Apparatus according to claim 17 in which the primary sensing means is fixed and the secondary sensing means are moved by the drive means.

19. Apparatus according to claim 17 in which the secondary sensing means are fixed and the primary sensing means is moved by the drive means.

20. A method of sampling material travelling past a sampling region across which a plurality of sensing means are arranged at spaced intervals, the sensing means having respective sensing zones in the sampling region, the method including the steps of causing relative periodic movement between the sensing means and the sampling region, or between at least one of the sensing means and the remaining sensing means so that, in a cycle of movement, there is a periodic overlap of at least the sensing zones of adjacent sensing means in the sampling region due to an overlap of respective scanning paths of the sensing means; producing monitoring signals when sensing respective adjacent portions of the travelling material across its width, the monitoring signals representing a characteristic of the travelling material; and processing the monitoring signals to provide an output for monitoring changes in said characteristic, the method further including using at least one of the sensing means as a primary sensing means for producing comparatively accurate monitoring signals compared with the monitoring signals produced by the other or secondary sensing means; and by storing and comparing the monitoring signals, or values corresponding thereto, which are produced where the scanning paths overlap, and producing information from said signals or values either for calibrating the secondary sensing means with respect to the primary sensing means and the material travelling past the sensing zone, or for making any one of the sensing means redundant, or both.

21. A method according to claim 20 wherein the second sensing means are of relatively lower quality than the primary sensing means and the calibration of the secondary sensing means is continuously updated by said information.

22. A method according to claim 21 in which the cyclic movement is such that the sensing zone of said primary sensing means traces out a scanning path which periodically covers reference means (9) as well as a portion of the scanning path of one of the secondary sensing means; the monitoring signals derived from said primary sensing means, when its sensing zone covers the reference means, being processed for calibrating the secondary sensing means.

23. A method according to claim 20 in which the cyclic movement is such that scanning paths of the sensing zones of adjacent sensing means overlap by an extent to provide redundancy in any one of the sensing means, the signal processing being such as to disregard a redundant sensing means.

24. A method according to claim 20, wherein the signal processing includes storing the monitoring signals or corresponding values derived from each of the sensing means over a predetermined number of cyclic movements, averaging said signals or values, and making computations based on the averages for the purpose of comparison and calibration.

25. A method according to claim 20, wherein the signal processing includes storing sets of monitoring signals for a multiplicity of scanning zones in fully interleaved scanning tracks of adjacent sensing means, averaging the monitoring signals stored over one or more cycles of movement, for making comparisons of average values, and computing variances for the purpose of calibration.

* * * * *